(12) United States Patent
Hindmarsh et al.

(10) Patent No.: US 11,590,275 B2
(45) Date of Patent: Feb. 28, 2023

(54) APPARATUS AND METHOD FOR THE TREATMENT OF DEFECTS INTERNAL OF THE BODY

(71) Applicants: CAMBRIDGE UNIVERSITY HOSPITAL NHS FOUNDATION TRUST, Cambridge (GB); CAMBRIDGE ENTERPRISE LIMITED, Cambridge (GB)

(72) Inventors: Andrew Hindmarsh, Cambridge (GB); Thomas Stone, Cambridge (GB); Daniel Marsden, Cambridge (GB); Pierre Lao-Sirieix, Cambridge (GB)

(73) Assignees: Cambridge Enterprise Limited, Cambridge (GB); Cambridge University Hospitals NHS Foundation Trust, Cambridge (GB)

( * ) Notice: Subject to any disclaimer, the term of this patent is extended or adjusted under 35 U.S.C. 154(b) by 562 days.

(21) Appl. No.: 16/094,447

(22) PCT Filed: Apr. 21, 2017

(86) PCT No.: PCT/GB2017/051123
§ 371 (c)(1),
(2) Date: Oct. 17, 2018

(87) PCT Pub. No.: WO2017/182827
PCT Pub. Date: Oct. 26, 2017

(65) Prior Publication Data
US 2019/0117857 A1    Apr. 25, 2019

(30) Foreign Application Priority Data

Apr. 21, 2016 (GB) .................................... 1606986

(51) Int. Cl.
*A61M 1/00* (2006.01)
*A61M 27/00* (2006.01)
(Continued)

(52) U.S. Cl.
CPC .............. *A61M 1/84* (2021.05); *A61M 25/09* (2013.01); *A61M 27/00* (2013.01);
(Continued)

(58) Field of Classification Search
CPC .... A61M 1/008; A61M 1/0023; A61M 25/09; A61M 27/00; A61M 25/005;
(Continued)

(56) References Cited

U.S. PATENT DOCUMENTS 3,595,241 A * 7/1971 Sheridan ........... A61M 25/0068
604/267
3,935,863 A * 2/1976 Kliger ..................... A61F 13/38
604/369

(Continued)

FOREIGN PATENT DOCUMENTS

DE   102009043472 A1   3/2011
EP       1572286 B1    5/2009
(Continued)

OTHER PUBLICATIONS

Search Report for Application No. GB1606986.6 dated Sep. 26, 2016.
(Continued)

*Primary Examiner* — Adam Marcetich
(74) *Attorney, Agent, or Firm* — ri Haynes Boone LLP

(57) ABSTRACT

A catheter for treatment of a defect internal of a human or animal body. The catheter may comprise a tube adapted for insertion into the body; an applicator disposed within and moveable relative to the tube; and a porous medium attached to the applicator; wherein the porous medium is capable of (Continued)

fitting inside the tube, whereby the applicator can be controlled at a proximal end of the tube to deploy the porous medium from a distal end of the tube so as to treat the defect.

23 Claims, 6 Drawing Sheets

(51) Int. Cl.
    *A61M 25/09* (2006.01)
    *A61M 25/00* (2006.01)
(52) U.S. Cl.
    CPC ..... *A61M 25/005* (2013.01); *A61M 2025/091* (2013.01); *A61M 2025/09183* (2013.01)
(58) Field of Classification Search
    CPC .. A61M 2025/091; A61M 2025/09183; A61M 1/84; A61M 1/90; A61F 13/36; A61F 13/38; A61F 13/00068; A61B 2217/005
    See application file for complete search history.

(56) References Cited

U.S. PATENT DOCUMENTS

| | | | | |
|---|---|---|---|---|
| 5,211,636 | A * | 5/1993 | Mische | A61M 25/09 600/585 |
| 5,401,247 | A * | 3/1995 | Yoon | A61B 10/0233 604/164.12 |
| 5,462,523 | A * | 10/1995 | Samson | A61M 25/0043 604/246 |
| 5,628,733 | A * | 5/1997 | Zinreich | A61M 27/00 604/267 |
| 5,843,017 | A * | 12/1998 | Yoon | 604/22 |
| 5,954,682 | A * | 9/1999 | Petrus | A61F 13/38 604/11 |
| 6,270,484 | B1 * | 8/2001 | Yoon | A61B 17/3494 604/264 |
| 10,792,403 | B2 * | 10/2020 | Benedict | A61M 1/85 |
| 2001/0025155 | A1 * | 9/2001 | Yoon | A61M 25/10 604/1 |
| 2005/0043678 | A1 * | 2/2005 | Freyman | A61M 25/1029 604/103.01 |
| 2006/0024641 | A1 * | 2/2006 | Mahlmann | A61C 17/08 433/91 |
| 2006/0116712 | A1 * | 6/2006 | Sepetka | A61B 17/12172 606/200 |
| 2006/0199147 | A1 * | 9/2006 | Mahlmann | A61C 17/096 433/96 |
| 2007/0255175 | A1 * | 11/2007 | Sangha | A61B 10/02 600/572 |
| 2011/0159457 | A1 * | 6/2011 | Offermann | A61B 5/417 433/91 |
| 2013/0035628 | A1 * | 2/2013 | Garrison | A61M 60/268 604/8 |
| 2014/0081246 | A1 * | 3/2014 | Johnson | A61M 1/0092 604/543 |
| 2014/0088529 | A1 * | 3/2014 | Bengtson | A61F 13/36 604/385.01 |
| 2014/0276625 | A1 * | 9/2014 | Jenkins | A61M 3/0279 604/514 |
| 2014/0276627 | A1 * | 9/2014 | Jenkins | A61B 17/24 604/514 |
| 2015/0148785 | A1 * | 5/2015 | Kleiner | A61M 1/84 604/543 |
| 2015/0250979 | A1 | 9/2015 | Loske | |
| 2016/0206369 | A1 * | 7/2016 | Frech | A61M 1/916 |
| 2016/0220741 | A1 * | 8/2016 | Garrison | A61B 17/22 |
| 2016/0296382 | A1 * | 10/2016 | Spillane | A61F 13/36 |
| 2016/0361477 | A1 * | 12/2016 | Loske | A61M 1/0023 |
| 2017/0000992 | A1 * | 1/2017 | Matlock | A61M 25/0097 |
| 2017/0035949 | A1 * | 2/2017 | Loske | A61B 17/42 |
| 2017/0165122 | A1 * | 6/2017 | Ide | A61F 9/007 |

FOREIGN PATENT DOCUMENTS

| | | | |
|---|---|---|---|
| EP | 1960030 B1 | 6/2010 | |
| JP | 2001252349 A | 9/2001 | |
| WO | 2004/041346 A1 | 5/2004 | |
| WO | 2007/064832 A1 | 6/2007 | |
| WO | 2009/115543 A1 | 9/2009 | |
| WO | WO-2011038949 A1 * | 4/2011 | ......... A61M 1/0023 |
| WO | 2014/169135 | 10/2014 | |

OTHER PUBLICATIONS

Kuehn, "Surgical Endoscopic Vacuum Therapy for Defects of the Upper Gastrointestinal Tract,"(2016) J Gastrointest Surg 20:237-243.
Annex to Form PCT/ISA/206 Communication Relating to the Results of the Partial Search International Search for PCT Application No. PCT/GB2017/051123, dated Aug. 17, 2017.
Provisional Opinion Accompanying the Partial Search Result for PCT Application No. PCT/GB2017/051123.
B. Braun, "Eso-SPONGE" product information PDF B26902 1014-1-1, available at https://www.bbraun.co.uk/en/products-and-therapies/laparoscopic-surgery/laparoscopic-document-library/eso-sponge-document-library.html, English translation of German document sited in UKIPO search report for Application No. GB1606986.6, accessed on Sep. 22, 2016.

* cited by examiner

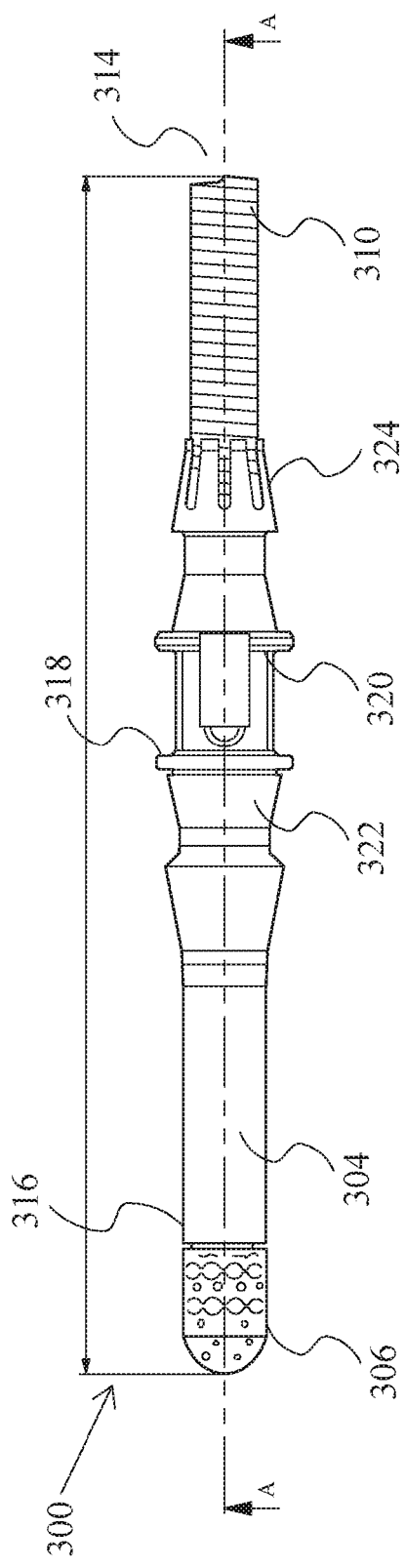
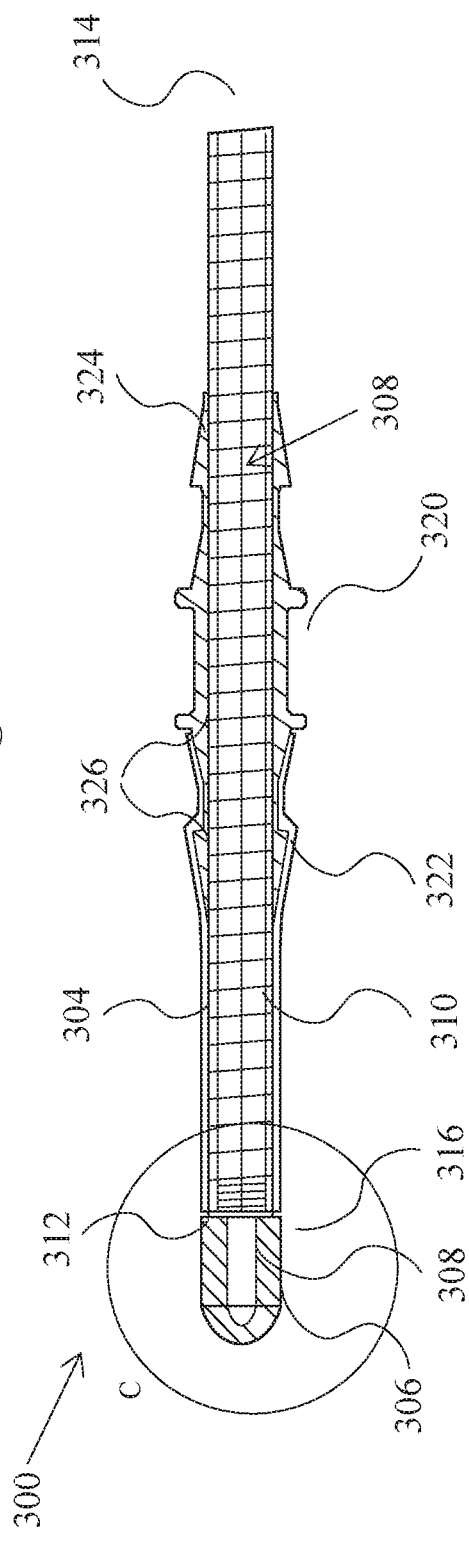
Fig. 4A
Fig. 4B

Detail C

APPARATUS AND METHOD FOR THE TREATMENT OF DEFECTS INTERNAL OF THE BODY

The invention relates to the treatment of defects internal of the human or animal body, such as abscesses and abscess cavities.

More specifically, the invention provides apparatus and methods for treating such internal defects through the application of a negative pressure at the site of the defect, for example to assist closure of an abscess cavity and/or to remove bodily fluids that may have accumulated at the defect.

Abscess cavities may include breaches in the continuity of the wall of the upper and lower gastrointestinal (GI) tract, which can create internal defects known as 'leak cavities'. Such breaches may be a result of anastomotic leak or spontaneous/iatrogenic perforation, which can often result in severe sepsis. Traditionally, open surgery and/or radiological drainage is required to treat such defects, though this approach is often associated with high rates of morbidity and mortality, and furthermore may not always be feasible. It is estimated that around 50% of patients who have a leak from the upper gastrointestinal (GI) tract that requires surgical intervention do not recover.

Abscesses occurring in the peritoneal and pleural cavities usually occur due to bacterial infection within that cavity, for example following visceral perforation in the peritoneal cavity, such as perforated appendicitis or perforated diverticulitus, or following pneumonia or other insult such as penetrating trauma in the pleural cavity. It is recognised that drainage of the cavity (i.e. removing contaminants) can help to control infection at these internal defects, though drainage by way of surgery is associated with increased morbidity and mortality.

It is desirable to provide an apparatus and method for treating such internal defects that may avoid the need for open surgery.

According to an aspect of the invention there is provided a catheter for treatment of a defect internal of a human or animal body, the catheter comprising: a tube adapted for insertion into the body; an applicator disposed within and moveable relative to the tube; and a porous medium attached to the applicator; wherein the porous medium is capable of fitting inside the tube, whereby the applicator can be controlled at a proximal end of the tube to deploy the porous medium from a distal end of the tube so as to treat the defect.

The defect may be an abscess cavity, possibly caused by a breach in the wall of the lower or upper gastrointestinal (GI) tract, including in the pharynx and oesophagus, whereby the catheter may be adapted for insertion into the body to access the defect endoluminally.

Alternatively, the defect may be an abscess in the peritoneal and pleural cavity, possibly caused by bacterial infection, whereby the catheter may be adapted for insertion into the body to access the defect percutaneously, and optionally using radiological guidance.

The apparatus may further be suitable for drainage, such as for drainage of an abscess cavity, whether in the abdominal or thoracic cavity, optionally wherein the catheter is arranged to be inserted percutaneously.

Thus, the catheter may be utilised to place the porous medium into the defect, optionally under endoscopic visualisation or radiological guidance, depending on the defect. By attaching the porous medium to the moveable applicator, instead of the tubing, it may be possible to deliver the end of tube to the site of a defect before deploying the porous medium, and then subsequently deploying the porous medium. The porous medium may also be retracted back into the tube using the applicator to allow it to be removed at the end of the treatment. In addition, it may be possible to use the applicator to control and adjust the extent to which the porous medium is deployed, e.g. into a defect cavity, once the catheter is in situ.

Optionally, the porous medium may be capable of being deformed such that it can fit inside the tube, and the porous medium may be arranged to return to its pre-deformed shape when deployed from the tube. Optionally, the porous medium may initially, prior to deployment, be contained within the tube, for example in a deformed (for example, compressed or 'non-expanded') state.

Optionally, the tube may be arranged to provide a fluid conduit, for example for application of a negative pressure to the deployed porous medium and/or for flushing of liquid into the cavity and/or for drainage purposes. Optionally, the applicator may be arranged to provide structural support to the tube, for example to inhibit the tube from collapsing and/or kinking.

Optionally, the applicator may be moveable in a longitudinal direction, for example wherein the amount of movement may be varied to control the amount of porous medium deployed. Optionally, the applicator may be a guidewire, for example a coiled guidewire having an internal bore. Optionally, the porous medium may be attached to the distal end of the applicator.

Optionally, the porous medium may be attached to the end of the applicator by a cord, thread, adhesive, heat-shrink wrap, or other suitable attachment means, whereby a first end of the cord may be secured to the porous medium and a second end of the cord may be secured to the applicator at a position spaced from the porous medium, such that the cord extends at least partway along the length of the applicator. Optionally, the second end of the cord may be attached to the applicator at a position that is external to the tube. Optionally, the porous medium may be attached to the end of the applicator by a suture.

Optionally, the porous medium may comprise a foam material such as an open-cell foam, which may comprise polyurethane. For example, a suitable open-cell foam may be a 'vacuum assisted closure' foam, VAC (REGISTERED TRADEMARK).

Optionally, the porous medium may comprise bio-active material, for example a bio-active collagen. The porous medium may be carried on the applicator and held in place either by friction, or by an additional binding such as an adhesive, or by wrapping it around the applicator or by mechanical fixing means, for example. Optionally, the porous medium may comprise a material designed to treat a cavity and/or restore continuity of a wall.

Optionally, the porous medium may be a tangled mesh of wire capable of being unravelled, stretched or drawn out into one or more single strands, the wire being arranged to have resilience causing it to reform the mesh when not restrained and/or under tension. Optionally, the porous medium may comprise a nickel titanium alloy, for example nitinol.

Optionally, the distal end of the tube may be arranged to provide a flared opening, for example a conical-shaped opening. Optionally, the tube may comprise fluorinated ethylene propylene (FEP). Optionally, the tube may be configured for nasogastric intubation.

Optionally, the catheter may further comprise an adaptor arranged to fit the applicator and provide a detachable fluid connection between the tube and a fluid flow generator capable of applying a negative pressure to the tube, for example a vacuum apparatus or a pumping apparatus. Optionally, the adaptor is arranged to provide a luer-lock connection with the fluid flow generator. The adaptor may also be used to couple a fluid source to the lumen of the catheter, for example to supply a fluid such as saline to the working (distal) end of the catheter to flush the defect and/or for example to deliver antibiotics.

Optionally, for insertion endoluminally, the catheter (or tube) may have an outer diameter arranged to fit within the working channel of an endoscope. For example, an endoscope having a working channel of 2.8 mm diameter would, preferably, require a catheter to have an outer diameter of less than 2.8 mm. For example, an endoscope having a working channel of 3.7 mm would, preferably, require a catheter having a working channel of less than 3.7 mm. Preferably, a clearance gap is required to allow movement of the catheter within the working channel of an endoscope—which typically has an internal diameter of about 3.7 mm or 2.8 mm—otherwise even so-called 'low friction' plastics (such as PVC, for example) may present a problem due to the length of channel and catheter. Optionally, for endoluminal insertion, the catheter (or tube) exterior may comprise a very smooth, preferably 'ultra-smooth', and/or a low-friction material, such as PVC (e.g. a material having a low friction coefficient), at least on its exterior surface.

Optionally, the length of the catheter may be at least 50% longer, and preferably at least 100% longer, than the length of the endoscope. Preferably, the catheter is flexible, and optionally it is sufficiently flexible to undergo a 1 cm diameter 180 degrees bend.

Optionally, for percutaneous insertion, the catheter may be arranged to be deployed along a guidewire arranged to guide the catheter into position within the body. The guidewire may be introduced to the body using a needle (or cannula). Preferably, the outer diameter of catheter is not specifically restricted for percutaneous use, such as may be necessary if the catheter is for endoluminal insertion, for example. Optionally, however, if the catheter is to be placed into a deep cavity between other structures, the catheter (or tube) may have an outer diameter similar to the outer diameter of the catheter for endoluminal insertion, and, for example, less than about 5 mm. The catheter for percutaneous insertion may have a similar rigidity to the endoscopic catheter. Optionally, the catheter may have a length of between about 20 and about 50 cm. Optionally, the catheter may comprise a low-friction material similar to the material of the catheter for endoluminal insertion.

Optionally, the catheter may be radio-opaque to aid x-ray guided visualisation of its insertion. Optionally, at least part of the applicator may be radio-opaque, for example if it comprises a metal or another suitably radio-opaque material.

According to another aspect of the invention there is provided a method for treating a defect, such as a leak cavity caused by a breach in a wall, of the lower or upper gastrointestinal (GI) tract internal of a human or animal body, the method comprising: introducing a catheter containing a deployable porous medium into the body, for example via endoluminal insertion; positioning the catheter at the defect (for example in an opening of a leak cavity, or adjacent the opening and preferably close enough to allow the porous medium to be deployed into a leak cavity); deploying the porous medium from the catheter; placing the porous medium into the defect; and applying a continuous negative pressure via the catheter to treat the defect.

Optionally, the catheter may be positioned using endoscopic visualisation. Optionally, the porous medium may be applied to the wall of the gastro-intestinal tract outside of the defect. Negative pressure can then be applied to the wall of the gastro-intestinal tract around the defect whereby to close the defect and/or inhibit the entry of bowel contents and other contaminants into the defect so as to assist healing.

According to another aspect of the invention there is provided a method for treating a defect, such as an abscess in a peritoneal or pleural cavity internal of a human or animal body, the method comprising: inserting a guidewire into the body, the guidewire being positioned at the site of a defect (for example at an abscess or infection having collection of fluid); inserting a catheter containing a deployable porous medium into the body percutaneously, wherein the catheter is deployed along the guidewire arranged to position the catheter at the defect; deploying the porous medium from the catheter; placing the porous medium into the defect; and applying a continuous negative pressure via the catheter to treat the defect.

Optionally, imaging guidance, for example ultrasound, may be used to position the guidewire at the defect. Optionally, the positioning of the guidewire may be checked using imaging, for example radiology.

Optionally, the porous medium may be initially contained within the catheter in a deformed state, whereby deployment of the porous medium causes it to return to its pre-deformed state.

Optionally, the catheter may comprise an applicator controllable to deploy the porous medium, the method further comprising controlling the applicator at a proximal end of the catheter to deploy the porous medium at a distal end of the catheter.

Optionally, the negative pressure applied may be less than 125 mm Hg, for example less than 100 mm Hg, for example less than 85 mm Hg.

According to another aspect of the invention there is provided a method of treating a defect, comprising using a catheter as described above with a method as described above.

According to another aspect of the invention there is provided a system for treating a defect internal of a human or animal body, the system comprising: a catheter as described above; and a fluid flow generator adapted to provide a fluid connection with the catheter, such that, when fluidly connected, a negative pressure can be applied by the fluid flow generator, via the catheter, to treat the defect.

According to another aspect of the invention there is provided a system for treating a defect internal of a human or animal body, the system comprising: a catheter, an elongate element disposed within and moveable relative to the catheter, and a porous substrate attached to an end of the elongate element, such that the porous substrate can be deployed from the catheter by advancing the elongate element at a position remote from the porous substrate; and a vacuum apparatus adapted to be fluidly connected to the catheter whereby to apply a negative pressure via the catheter to treat the defect.

Optionally, the system further comprises an endoscope capable of positioning the catheter at the defect under endoscopic visualisation.

Optionally, the system further comprises visualisation means for positioning the catheter at the defect.

Optionally, the system may be arranged such that the catheter is deployed alongside the endoscope, for example wherein the catheter may be attachable to the endoscope, such that it can be positioned at a defect with the endoscope. Alternatively, the catheter may be arranged to fit within the lumen of the endoscope, such that it can be positioned at a defect with the endoscope.

Optionally, the system further comprises a guidewire and insertion needle (or cannula) arranged to insert the guidewire into the body.

Optionally, the system may be arranged such that the catheter is deployed along a guidewire introduced into the body percutaneously so as to position the catheter at a defect.

Optionally, the guidewire may pass through the catheter or it may run alongside the catheter.

A fluid source may be connectable to the lumen of the catheter, for example to supply a fluid such as saline to the working (distal) end of the catheter to flush the defect and/or for example to deliver antibiotics.

Miniaturisation may allow the catheter to be used in other areas of the body.

According to another aspect of the invention there is provided a kit of parts for a catheter, comprising an applicator and a porous medium attached to an end of the applicator.

Optionally, in the kit, the applicator may be a guidewire, for example a coiled guidewire having an internal bore. Optionally, in the kit, the porous medium may be attached to the end of the applicator by a suture. Optionally, in the kit, a first end of the suture thread (or cord) may be secured to the porous medium and a second end of the suture thread (or cord) may be secured to the applicator at a position spaced from the porous medium, such that the suture thread (or cord) may extend at least partway along the length of the applicator.

Optionally, the kit may further comprise a tube arranged to fit over the applicator so as to provide a fluid conduit. Optionally, the kit may further comprise an adaptor for coupling the tube to a vacuum apparatus, the adaptor arranged to allow the applicator to pass therethrough.

Optionally, the kit may further comprise a guidewire and a needle or cannula for inserting the guidewire into a body, preferably wherein the guidewire is arranged so as to pass through the applicator whereby to enable percutaneous insertion of the catheter into the body via the guidewire.

According to another aspect of the invention there is provided a substrate for delivering bio-active material into an internal wound in a human or animal body, the substrate (for example, an extensible substrate) carrying a bio-active material, wherein the substrate is configured at least partially to shed the bio-active material into a wound.

Optionally, the substrate may be flexible. Preferably, the substrate is more flexible than the bio-active material such that flexure of the substrate causes shedding of the bio-active material.

Optionally, the substrate is elongate and configured to form a mesh when not restrained and/or under tension. Optionally, the elongate substrate may be arranged to form a resilient mesh when not restrained and/or under tension. Optionally, the substrate may comprise a wire or tape. Optionally, the substrate may comprise a memory metal, such as nitinol. Optionally, the bio-active material may comprise collagen.

Optionally, the bio-active material may be water soluble. Optionally, the bio-active material may be adhered to the substrate by a water-soluble adhesive.

According to another aspect of the invention there is provided a method of delivering bio-active material into an internal wound in a human or animal body, comprising: positioning a catheter at the wound; and deploying an extensible substrate from the catheter into the wound; wherein said substrate carries the bio-active material and is configured to at least partially shed the bio-active material into the wound.

Optionally, the substrate may be deployed from a distal end of the catheter positioned at the wound. Optionally, deployment of the substrate may be controlled from a proximal end of the catheter. Optionally, the substrate may shed bio-active material while extended from the catheter, for example during deployment or during retraction.

Optionally, the distal end of the catheter may be configured to cause at least some of the bio-active material to shed from the substrate into the wound as the wire is retracted back into the catheter, for example wherein the distal end has serrations. Optionally, the substrate is elongate and configured to form a mesh when not restrained by the catheter and/or under tension.

Optionally, the elongate substrate may be arranged to form a resilient mesh when not restrained by the catheter and/or under tension. Optionally, the substrate may comprise a wire or tape. Optionally, the substrate may comprise a memory metal, such as nitinol. Optionally, the bio-active material may comprise collagen.

Optionally, the substrate may be flexible. Preferably, the substrate is more flexible than the bio-active material such that flexure of the substrate causes shedding of the bio-active material.

Optionally, the bio-active material may be water soluble. Optionally, the bio-active material may be adhered to the substrate by a water-soluble adhesive.

As used herein, the term "abscess" preferably connotes a drainable, infected fluid collection.

As used herein, the terms "vacuum apparatus" and "fluid flow generator" preferably include apparatus arranged to generate a vacuum, or at least a negative pressure (i.e. suction) via a tube or catheter.

As used herein, the term "proximal" preferably connotes situated nearer to a point of attachment, to an apparatus for example. In contrast, the term "distal" preferably connotes situated away (or remote) from a point of attachment, to an apparatus for example.

As used herein, means plus function features may be expressed alternatively in terms of their corresponding structure.

Any apparatus feature as described herein may also be provided as a method feature, and vice versa. Furthermore, any feature in a particular aspect of the invention may be provided independently and/or applied to other aspects of the invention, in any appropriate combination.

An exemplary embodiment of the invention will now be described with reference to the accompanying figures, in which:

FIGS. 4A and 4B show a side view and a cross-sectional side view (A-A) of the catheter;

Endoscopic vacuum therapy (EVT) is a relatively new technique for treating defects, such as oesophageal perforation and certain other post-operative leakages. EVT is a minimally invasive, alternative method of treatment to traditional surgery, utilising vacuum-assisted closure (VAC) techniques.

EVT involves placing a polyurethane sponge into a defect cavity under endoscopic visualization and then applying a continuous negative pressure, causing the cavity to collapse around the sponge. The sponge is typically changed every 48-72 hours until the cavity shrinks and stable granulation tissue forms a barrier.

Devices used for EVT are typically 'homemade' and therefore quite crude in their construction, and could be improved. For example, one treatment method involves a nasogastric tube first being inserted through the nose under general anaesthesia, and then the distal end pulled out through the mouth, and attached to a polyurethane sponge which has been cut to size. The polyurethane sponge may be secured to the nasogastric tube by suture. The sponge is then delivered (attached to the tube) to a defect by a tripod-equipped endoscope, under direct endoscopic visualisation.

Figure 1:
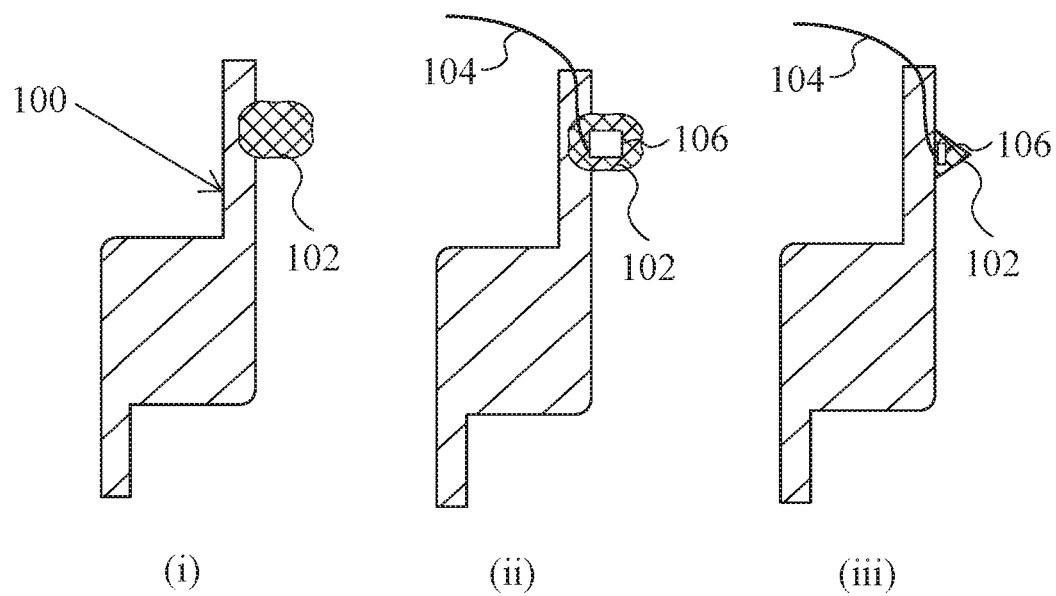
FIG. 1 shows different stages of endoscopic vacuum therapy (EVT)

Referring to FIG. 1, a schematic diagram of an oesophagus 100 is used to show an example of three different stages (i)-(iii) of endoscopic vacuum therapy (EVT) being used to treat a gastrointestinal defect. In this example, EVT is being used to treat a defect 102 in the oesophagus 100, as illustrated in (i). To treat the defect 102, a tube 104 may be inserted through the nose and then directed to the defect 102 under direct endoscopic visualisation, as illustrated in (ii). A sponge 106 attached to the tube 104 may be placed in the defect cavity. A negative pressure, such as −125 mm Hg for example, may then be applied, causing the defect 102 cavity to collapse around the sponge 106 to aid healing, as illustrated in (iii). This treatment may also be referred to as endoscopic 'transluminal' or 'intraluminal' vacuum therapy.

Figure 2:
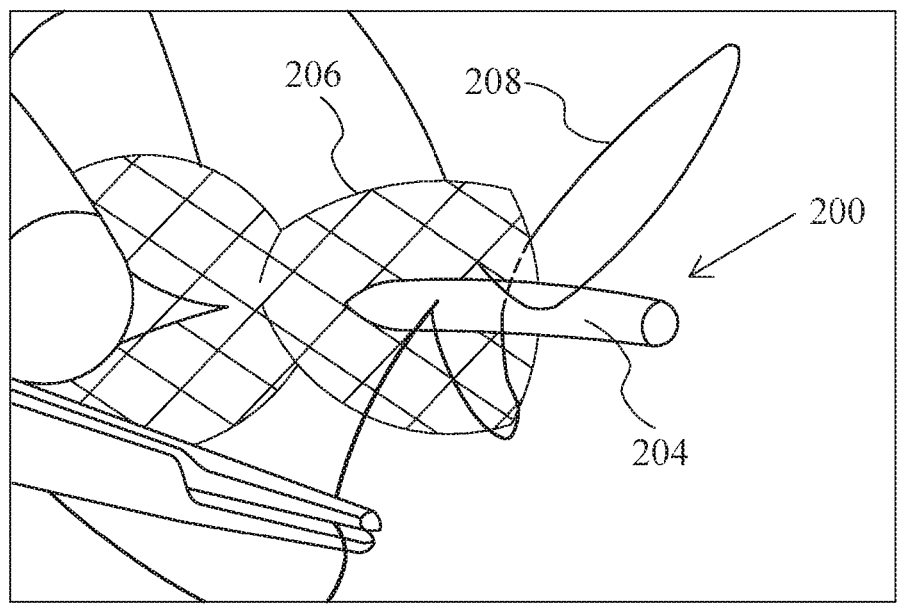
FIG. 2 shows a basic device for use with EVT.

Referring to FIG. 2, a basic apparatus 200 for use in endoscopic vacuum therapy may include a sponge 206 attached to an end of a tube 204 using a suture 208. The tube 204 may be 12-16 F nasogastric (feeding) tube. The sponge 206 may be polyurethane. The suture 208 may be made using '0 silk'. Due to the sponge 206 being in an expanded state, it cannot be passed down the working (or 'tool') channel of an endoscope but rather has to be secured to the outside of the endoscope for placement into a defect cavity, meaning placement of the sponge 206 can be difficult.

Figure 3:
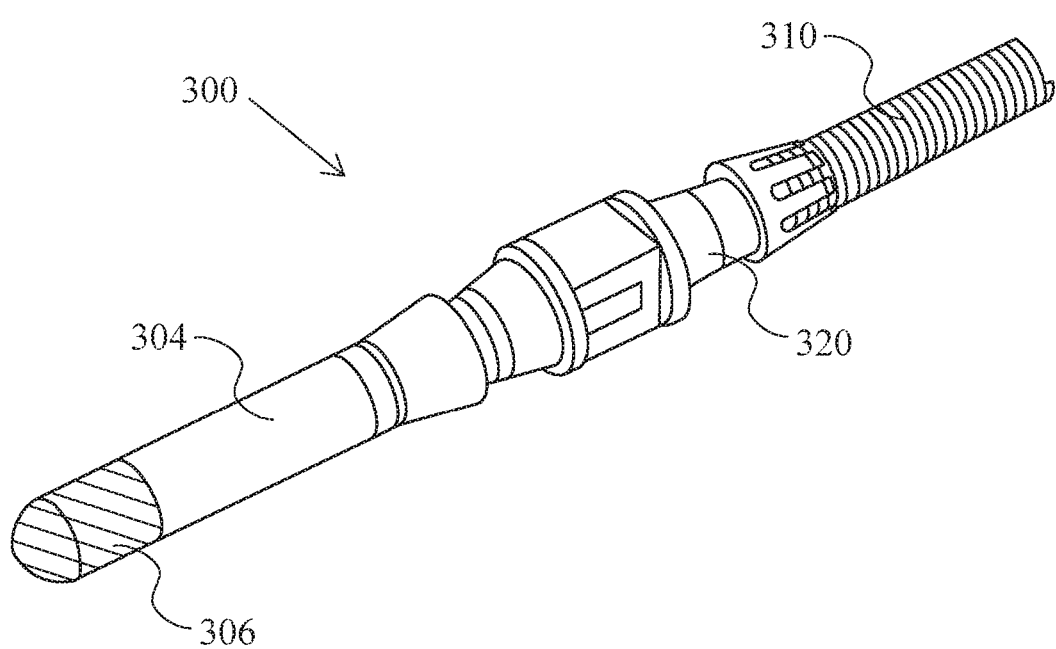
FIG. 3 shows an example of a catheter.

Referring now to FIG. 3, a catheter 300 may include a porous medium 306 secured to a distal end 312 (shown in FIG. 4B) of an applicator 310. The applicator 310 may be disposed at least partially within a tube 304. The tube 304 may have a distal end 316 and a proximal end 318 (as shown in FIG. 4B). The distal end 316 of the tube 304 and the distal end 312 of the applicator 310 may be substantially coincident.

The proximal end 318 of the tube 304 may be secured to an adaptor 320. The applicator 310 may be arranged to pass through the adaptor 320 into the tube 304. A distal end 314 of the applicator 310 may be arranged to extend out from the other side of the adaptor 320. The adaptor 320 may be arranged to provide a fluid connection with a vacuum apparatus (not shown). When the adaptor 320 is connected to a vacuum apparatus, a negative pressure may be applied to the porous medium 306 via the tube 304.

FIGS. 4A and 4B show the catheter 300 in side profile. FIG. 4B is a cross-sectional view of the catheter taken along line A-A as indicated in FIG. 4A.

The applicator 310 may be elongate. The applicator 310 may be sufficiently elongate (and of suitable diameter) that it can be inserted through a patient's nose. The applicator 310 may be arranged to provide flexibility without creating sharp kinks. The applicator 310 may be flexible while substantially maintaining an inner bore that can act as a fluid conduit. The applicator 310 may be metal, for example a stainless steel such as 304 or 316 stainless steel. The applicator 310 may have a diameter of less than 3.7 mm or 2.8 mm, so that it can fit inside a standard endoscope having an internal diameter of 3.7 mm or 2.8 mm. The applicator 310 may have a perforate or foraminous wall. The applicator 310 may be a guidewire. The guidewire may be a guide coil.

The applicator 310 may be moveable relative to the tube 304 in a longitudinal direction. The applicator 310 may also be moveable relative to the tube 304 in a rotational sense. The porous medium 306 may be deployed from a distal end 316 of the tube 304 by moving the applicator 310 in a longitudinal direction relative to the tube 304. The applicator 310 may be moved relative to the tube 304 by controlling the applicator 310 at a region of the applicator 310 that is not disposed within the tube 304 or adaptor 320. The applicator 310 may be controlled at a proximal end 314 of the applicator 310. The extent to which the porous medium 306 is deployed from the tube can be controlled by the applicator 310. The applicator 310 may have a measurement guide disposed on at least its proximal end 314 to aid deployment of the porous medium 306.

The tube 304 may fit closely over the applicator 310. The tube 304 may provide a fluid conduit between the adaptor 320 and the porous medium 306. The tube 304 may provide a fluid tight seal between the adaptor 320 and the porous medium 306. The tube 304 may be supported structurally by the applicator 310 to maintain a fluid conduit through the tube 304.

The distal end 316 of the tube 304 may be flared open (not shown) to aid retraction of the porous medium 306 back into the tube 304. The tube may have an external diameter that allows it to fit (and have relative movement) inside the working channel of a standard endoscope, preferably either less than 2.8 mm or less than 3.7 mm, depending on the endoscope.

The tube 304 may be a thin-walled polymer. The tube 304 may be a low-friction polymer, compared to silicon and/or PTFE. The tube 304 may have greater elasticity than PTFE. The tube 304 may be arranged to be resistant to kinking. The tube 304 may be capable of twisting or bending with a curvature of about 1 cm radius. The tube may be capable of bending greater than 90 degrees without rupturing or kinking. The applicator 310 may provide structural support that helps the tube 304 from kinking. The tube 310 may be formed from fluorinated ethylene propylene (FEP).

The adaptor 320 may have a first connector 322 (not shown) for connecting to the tube 304. The first connector 322 may be a "Christmas tree" connector. The first connector 322 may have one or more barbs 326. The tube 304 may be capable of being stretched to fit over the barbs 326 and sufficiently elastic that upon retraction it crimps over the barbs 326 to secure the tube 304 to the adaptor 320. The adaptor 320 may have a second connector 324 for connecting to a vacuum apparatus (not shown). The second adaptor 324 may be a 'luer lock' type connector. The adaptor may be substantially straight so that the first connector 322 and second connector 324 are substantially in-line. The adaptor 320 may be made from nylon or polycarbonate.

The porous medium 306 may be 'bullet-shaped'. Alternatively, the porous medium 306 may be "teardrop-shaped". Indeed, the porous medium 306 could take the form of many different 3D shapes, such as a cuboid, pentagonal prism and cylinder for example. The porous medium 306 may be resiliently deformable from a first state to a second state. The porous medium 306 may be deformable to the second state, and may further be maintained in that second state, under a compression force, provided by squeezing the porous medium by hand, for example. The porous medium 306 may return to the first state when the compression force is removed.

The porous medium 306 may be polyurethane foam. Alternatively, the porous medium 306 may be an expandable mesh, preferably a wire mesh. The mesh may be capable of being unravelled, stretched out, or drawn out into a single thread of wire and to return to its mesh form when released. The mesh may be formed of a shape-memory material. The mesh may be formed from a nickel titanium alloy. The mesh may be formed from nitinol.

Alternatively, the porous medium 306 may be formed from a bio-active material, such as bio-active collagen. The bio-active material may be arranged to degrade itself after a predetermined period of time. The bio-active material may be capable of being wrapped around the applicator 310 (or otherwise attached) to create a porous, sponge- or foam-like medium.

Prior to deployment, the porous medium 306 may be compressed within the tube 304. Upon deployment, a portion of the porous medium 306 that is no longer contained within the tube may expand or undeform back to its pre-deformed state.

Figure 5:
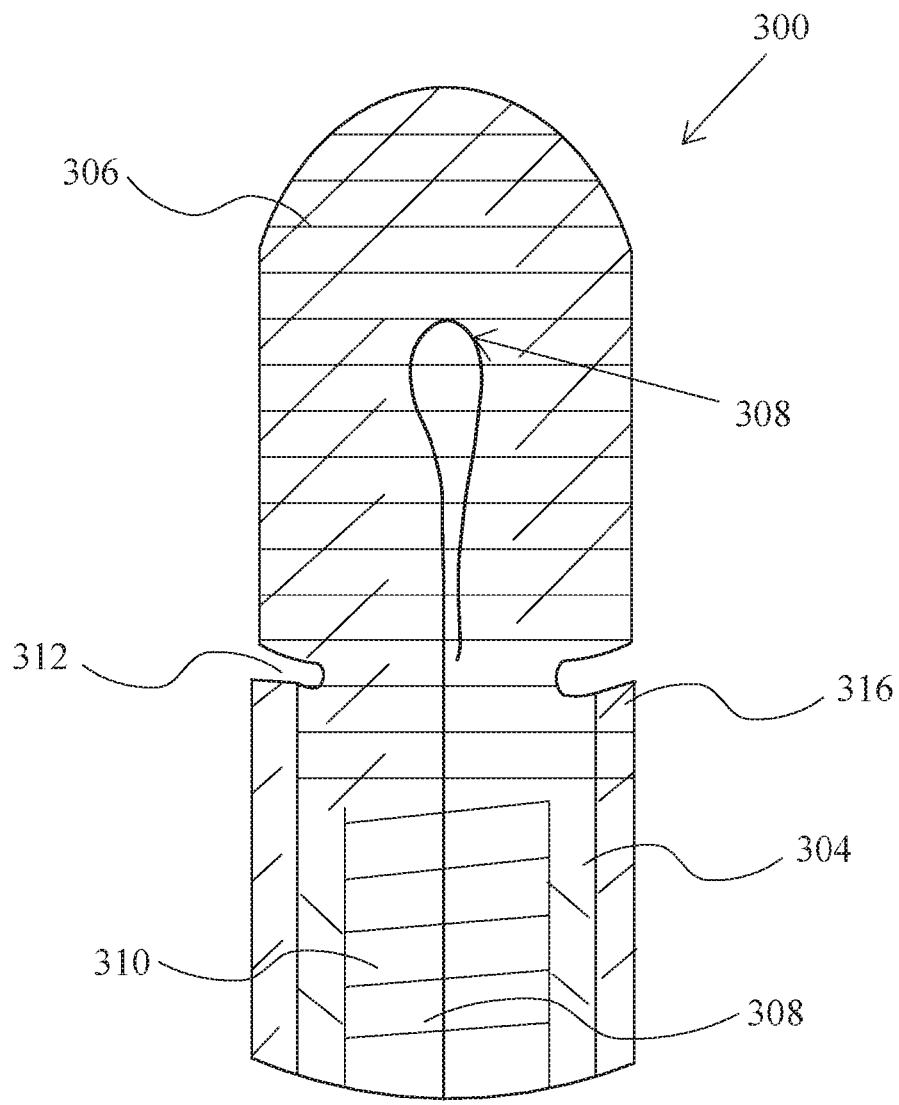
FIG. 5 shows a detailed view (C) of a porous medium secured to a distal end of the catheter.

Referring to FIG. 5, the porous medium 306 may be secured to the distal end 312 of the applicator 310 by way of a suture 308. The suture 308 may be secured to the applicator 310 at a point that is spaced-apart from the porous medium 306. The suture 308 may be secured to the applicator 310 at a point along the length of the applicator 310 that is not disposed within the tube 304 or adaptor 320, with the suture 308 passing either alongside or through the applicator 310. Alternatively, the porous medium 306 may be glued or otherwise secured to the applicator 310.

The catheter 300 as shown in FIGS. 3-5 is not shown to scale. The tube 304 may be of sufficient length to extend from outside of a patient's body to the defect 102 inside the patient's body. The tube 304 may have a length of between about 0.5 m and 1.5 m. The applicator 310 may be at least as long as the tube 304. In use, the adaptor 320 may be located outside of the patient's body. The portion of the applicator 310 that extends out of the adaptor 320 may be of sufficient length to be controlled to allow relative longitudinal movement within the tube 304 to allow deployment of the porous medium 306 from the distal end 316 of the tube 304. The applicator 310 may be allowed to move relative to the tube 304 a longitudinal distance of between 1-10 mm, for example. The size of the defect 102 will to a great extent dictate the amount of porous medium 306 to be deployed. Accordingly, the applicator 310 may be required to move longitudinally within the tube 304 by up to 50 mm, perhaps further.

For small defects 102, the porous medium 306 may be deployed within the lumen of a delivery endoscope, which may then be placed adjacent the defect 102 and a negative pressure applied to cause the wall tissue at the defect to be sucked into the lumen for treatment of the defect 102.

A skilled person will appreciate that the apparatus 200 shown in FIG. 2 differs from the catheter 300 shown in FIG. 3 at least because the apparatus 200 has a sponge 206 secured to the outside of the tube 204, which is therefore not a porous medium capable of fitting inside the tube 204, and further because there is no applicator disposed within the tube 204.

The catheter 300 may be inserted by attaching it to the outside of an endoscope. Alternatively, the catheter 300 may be deployed from within the working channel of an endoscope.

Once the catheter 300 has been inserted into a patient and correctly positioned, the porous medium 306 may be deployed from the distal end 316 of the tube 304 into a defect cavity 102 by advancing the applicator 310. A vacuum apparatus may then be connected to the adaptor 320 and a continuous negative pressure (i.e. suction) applied to the porous medium 306 via the tube 304. The negative pressure causes the defect cavity to collapse around the porous medium 306 to aid healing of the defect 102, as discussed above. Importantly, the porous medium 306 need only be deployed from the tube 304 once the catheter 300 has been correctly placed at a defect 102 after inserted into the patient's body.

The catheter 300 also allows the defect cavity 102 to be flushed out with fluid, if required and/or suction applied to remove bodily (or other) fluids, i.e. for drainage purposes, for example to remove contaminants from the defect cavity.

The endoscope may be removed while leaving the catheter 300 in-situ for a predetermined period of time. The applicator 310 may then be used again to retract the porous medium 306 back into the tube 304 before the catheter 300 is withdrawn from the patient's body. The catheter 300 can then be replaced, as required.

Thus, the applicator 310 may function as both a reinforcement mechanism to the tube 304 and a deployment mechanism providing controlled deployment of the porous means 306.

When the endoscope is withdrawn, the catheter 300 may be left extending out of a patient's mouth. In order to retract the catheter 300, a plastic tube may be inserted through the nose and reattached to the catheter 300, which can then be fed back up through and out from nose.

The porous medium 306 may not fill the defect cavity 102 entirely. Only a small amount of porous medium 306 may be required to initiate collapse of the defect cavity 102 and hence aid healing.

Standard endoscopes are generally available in two sizes: 2.8 mm and 3.7 mm diameter. The 2.8 mm diameter version is the more common type of endoscope, but this reduces the amount of porous medium 306 that can be deployed, hence using collagen for the porous medium 306, as described above, is of particular interest.

The catheter 300 is not limited for intraluminal treatment of the upper gastro-intestine (GI). The catheter 300 may also be used in treatment of the lower gastro-intestine (GI), such as for colonoscopy, for example, and for other parts of the body.

Alternatively, the catheter 300 may be introduced to a patient's body via percutaneous insertion, i.e. through the skin, similar to the method of inserting an intercostal chest drain, for example by performing a direct cut down, or using the 'Seldinger' technique. Thus the catheter 300 may be used to perform percutaneous drainage, for example to treat an abscess in the peritoneal or pleural cavity, and the abdominal or thoracic cavity, in addition to being used to treat internal defects, such as leak cavities, as discussed above.

The applicator 310 and/or porous medium 310 and/or tube 304 may be provided together in kit form for assembly when required.

Figure 6:
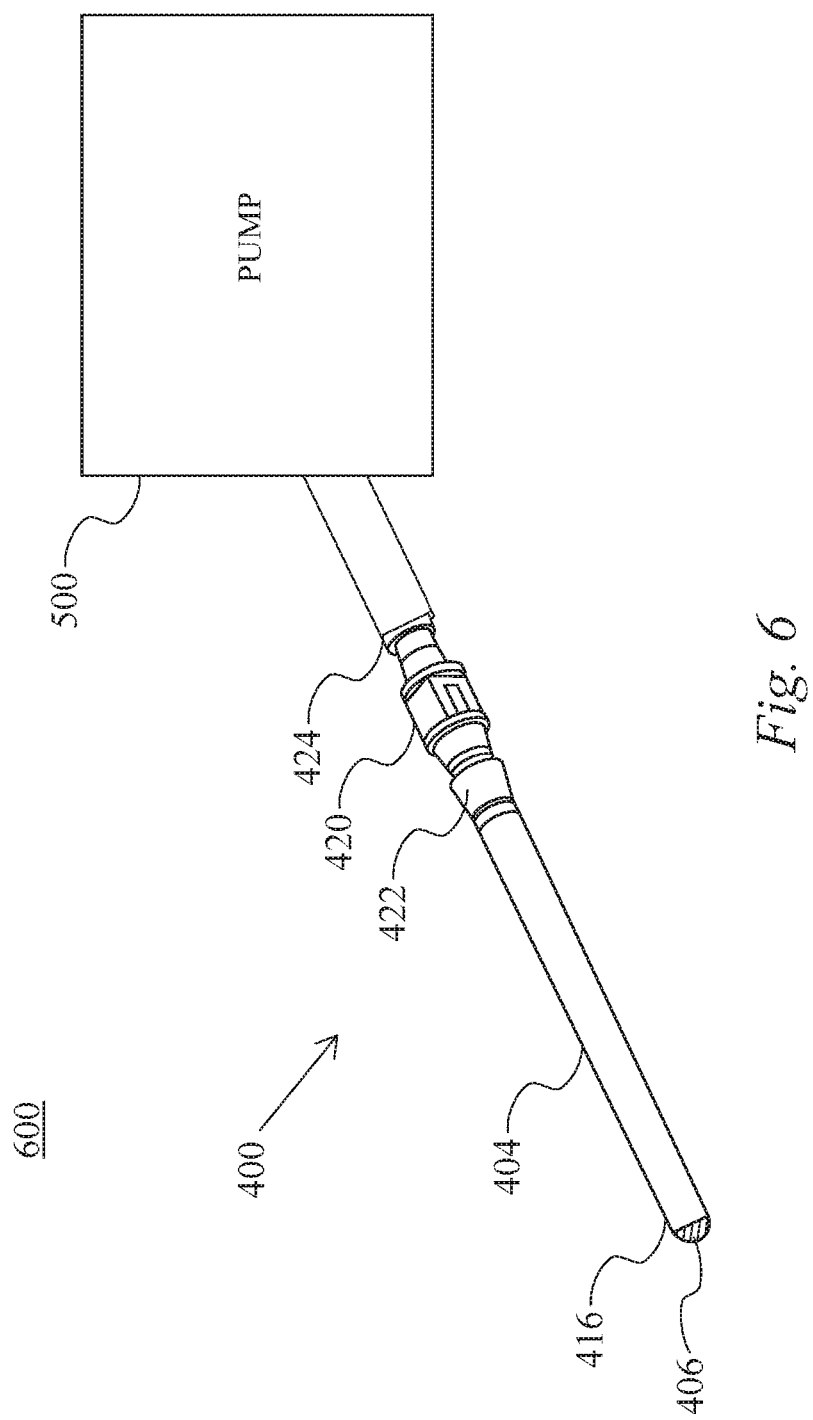
FIG. 6 shows a system for EVT.

FIG. 6 shows a system 400 for treating a defect according to an embodiment of the invention. The system 600 includes a catheter 400 and a vacuum apparatus 500 arranged to be fluidly connected together such that a negative pressure can be applied by the vacuum apparatus 500 via the catheter 400.

The catheter 400 includes an adaptor 420 provided with a luer lock connector 424 for coupling with the vacuum apparatus 500. The adaptor 420 is provided with a further connector 422, which is substantially in-line with the luer lock connector 424, for coupling with a flexible tube 404, formed from FEP. The further connector 422 is provided with barbs, which the flexible tube 404 is stretched over so as to provide a secure fluid-tight coupling.

Disposed within the tube, but not visible in this figure (refer to FIG. 3) is an applicator 410 that passes through the adaptor 420 and extends towards a distal end 416 of the tube 404. A porous medium 406, which is just about visible in FIG. 6, is secured, via suture, to the end of the applicator 410.

In this exemplary embodiment, the applicator 410 is a coiled guidewire, and the porous medium 406 is a teardrop-shaped polyurethane foam, which is sufficiently compressible to allow it to be compressed to fit within the tube 404 and sufficiently resilient that it can resume its uncompressed shape when deployed from (and hence no longer constrained within) the tube 404.

The applicator 410 is moveable in a longitudinal direction relative to the tube 404. The applicator 410 can therefore be controlled to advance the porous medium 406 towards the distal end 416 of the tube 404 and hence deploy it. As the porous medium 406 is deployed from the tube 404, it expands.

Thus, once the catheter 400 has been positioned at a defect cavity, and prior to connecting the catheter 400 to the vacuum apparatus 500, the applicator 410 can be controlled to deploy the porous medium 406. The vacuum apparatus 500 is arranged to connect to the luer lock connector 424 on the catheter 400 to provide a fluid connection to the porous medium 406 at the distal end of the catheter 400.

In use, once the catheter 400 has been inserted into a patient's body, via the nasal canal for example, and positioned by the defect, and the porous medium 406 deployed, the vacuum apparatus 500 may be attached to the catheter 400, via the adaptor 420, and a negative pressure (or 'suction') applied to the porous medium 406 via the tube 404, which is structurally supported by the coiled guidewire acting as the applicator 410.

Figure 7:
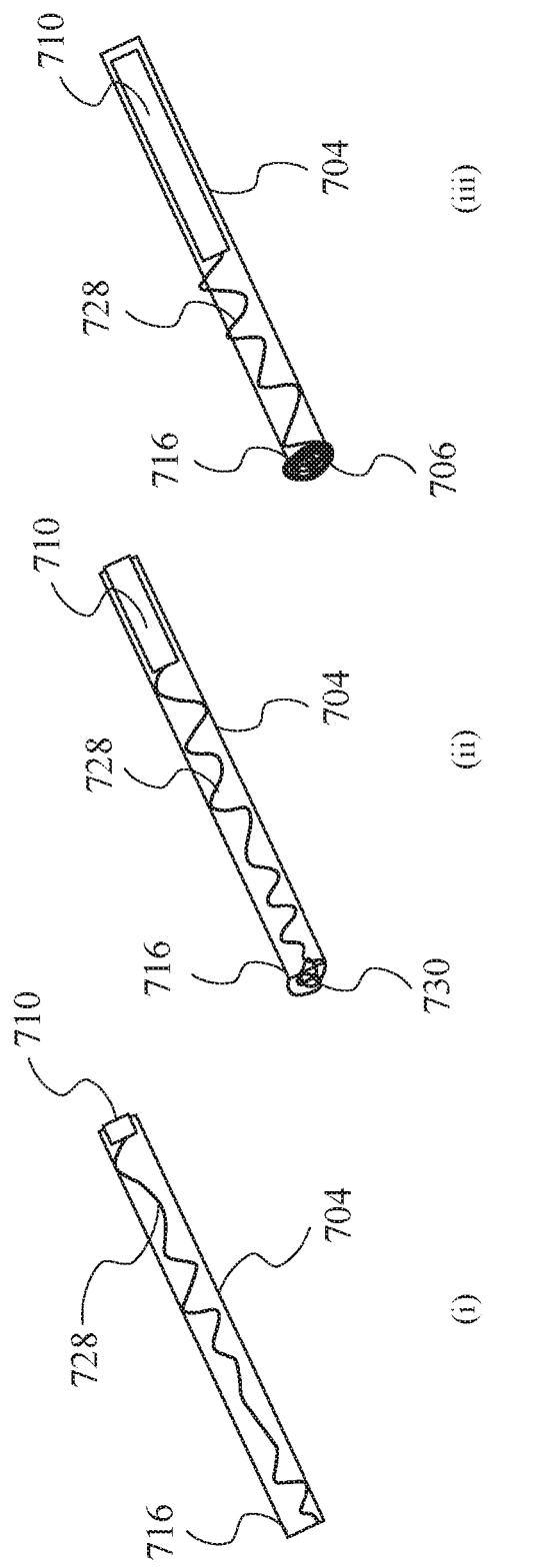
FIG. 7 shows an exemplary embodiment of a porous medium.

FIG. 7 shows various different stages of a porous medium 706 being formed of an expandable mesh (in an exemplary embodiment), which is capable of being unravelled, stretched out or drawn out into a single thread of wire 728 and of returning to its original mesh form 706 when released, being deployed from the distal end 716 of a tube 704 of a catheter.

As shown in the first (i) view, the wire 728 has been unravelled and is being held under tension in the tube 704 by the applicator 710. In the second view (ii) an amount of wire 728 has been released by advancement of the applicator 710 and allowed to deploy from the distal end 716 of the tube 704, where it is beginning to form a mesh 730. In the third (iii) view, a substantial amount of wire 728 has been released by further advancement of the applicator 710 and a mesh 730 has formed at the distal end 716 of the tube 704, suitable to provide a porous medium 706.

Where the porous medium 706 is provided by such a wire 728, the distance that the applicator 710 may be required to move within the tube 704 will of course be much further than if the porous medium 706 were a foam sponge, for example. Indeed, the applicator 710 may be required to travel substantially the entire length of the tube 704. The wire 728 may alternatively be a tape, or similar elongate element.

In another embodiment (not shown), a catheter (or other suitable apparatus) may contain an extensible substrate coated in a bio-active material, such as collagen. The bio-active material may be arranged to shed from the substrate, such that at least a portion of it can be deposited into an internal wound when the substrate positioned there by the catheter. The bio-active material may be particularly suitable for treating wounds or otherwise helping them to heal.

Similar to the arrangement described above, the substrate may comprise a wire, tape or similar elongate element that is formed into a mesh configuration. Furthermore, the substrate may be sufficiently resilient that if drawn or stretched out (such that the mesh is deformed) it will return to a resilient mesh configuration, or otherwise undergo flexure of some description, when no longer under tension and/or restrained within the catheter. The substrate may comprise a memory metal, such as nitinol. The substrate is, preferably, more flexible than the bio-active material coated onto it, such that flexure of the substrate causes the bio-active material to be shed. The bio-active material may be coated onto the substrate using a water-soluble adhesive. The bio-active material may itself be water-soluble.

A distal end through which the substrate can be deployed into a wound may be configured to cause the substrate to flex as it is either deployed or retracted. The distal end may be configured for example to cause the substrate to flex, or it may have features that cause the bio-active coating to shed, such as serrations. As described above, deployment of the substrate may be controlled from a proximal end of the catheter. The bio-active coating may shed either during deployment of the substrate into the wound or retraction of the substrate into the catheter. Indeed, the bio-active coating may shed during both procedures.

It will be understood that the present invention has been described above purely by way of example, and modifications of detail can be made within the scope of the invention.

The invention claimed is:

1. A catheter for treatment of a defect internal of a human or animal body, the catheter comprising:
   a tube adapted for insertion into the body;
   an applicator disposed within and moveable relative to the tube; and
   a porous medium attached to the applicator;
   wherein the porous medium is capable of fitting inside the tube,
   whereby the applicator can be controlled at a proximal end of the tube to deploy the porous medium from a distal end of the tube wherein, when fully deployed, the porous medium remains in contact with an inner surface of the tube for the application of negative pressure to the porous medium so that the porous medium can apply the negative pressure to a target tissue comprising the defect so as to treat the defect;
   wherein the tube is arranged to provide a fluid conduit for application of the negative pressure to the deployed porous medium.

2. The catheter of claim 1, wherein the porous medium is capable of being deformed such that it can fit inside the tube, and wherein the porous medium is arranged to retain its pre-deformed shape when deployed from the tube.

3. The catheter of claim 1, wherein the porous medium is initially, prior to deployment, contained within the tube.

4. The catheter of claim 1, wherein the tube is arranged to provide a fluid conduit for flushing of liquid into the cavity and/or for drainage purposes.

5. The catheter of claim 1, wherein the applicator is arranged to provide structural support to the tube.

6. The catheter of claim 1, wherein the applicator is moveable in a longitudinal direction relative to the tube.

7. The catheter of claim 1, wherein the applicator comprises a coiled wire and an internal bore.

8. The catheter of claim 1, wherein the porous medium is attached to the distal end of the applicator.

9. The catheter of claim 8, wherein the porous medium is attached by a thread or cord, whereby a first end of the thread or cord is secured to the porous medium and a second end of the thread or cord is secured to the applicator at a position spaced from the porous medium, such that the thread or cord extends at least partway along the length of the applicator.

10. The catheter of claim 9, wherein the second end of the thread or cord is attached to the applicator at a position along the applicator that is external to the tube.

11. The catheter of claim 1, wherein the porous medium is a tangled mesh of wire capable of being unravelled into one or more single strands, the wire being arranged to have resilience causing it to reform the mesh when not restrained and/or under tension.

12. The catheter of claim 1, wherein the porous medium comprises a bio-active material.

13. The catheter of claim 1, wherein the distal end of the tube is arranged to provide a flared opening.

14. The catheter of claim 1, further comprising an adaptor arranged to fit over the applicator and provide a detachable fluid connection between the tube and a fluid flow generator.

15. The catheter of claim 1, wherein the tube is configured for endoluminal insertion.

16. The catheter of claim 1, having an outer diameter of less than 3.7 mm.

17. The catheter of claim 1, wherein the tube is configured for percutaneous insertion.

18. The catheter of claim 17, further arranged to be deployed along a guidewire.

19. A system for treatment of a defect internal of a human or animal body, the system comprising:
a catheter according to claim 1; and
a fluid flow generator adapted to provide a fluidly connection with the catheter;
such that, when fluidly connected, a negative pressure can be applied by the fluid flow generator, via the catheter, to treat the defect.

20. The catheter of claim 1, wherein the applicator comprises a foraminous wall.

21. The catheter of claim 1 in kit form for assembly when required.

22. The catheter of claim 1 wherein the porous medium is a continuous porous medium that fills a volume.

23. The catheter of claim 1, wherein the applicator can be controlled at the proximal end of the tube to deploy the porous medium from the distal end of the tube so as to treat the defect by endoscopic vacuum therapy; and
wherein the tube is arranged to provide a fluid conduit for application of the negative pressure to the deployed porous medium deployed and placed into the defect.

* * * * *